United States Patent [19]

Spritzer et al.

[11] 4,329,214
[45] May 11, 1982

[54] GAS DETECTION UNIT

[75] Inventors: Lawrence Spritzer, Peekskill, N.Y.;
Joseph R. Stetter, Naperville, Ill.;
Donald R. Rutt, Merrick, N.Y.

[73] Assignee: Becton, Dickinson and Company, Paramus, N.J.

[21] Appl. No.: 170,368

[22] Filed: Jul. 21, 1980

[51] Int. Cl.³ .................. G01N 27/28; G01N 27/46
[52] U.S. Cl. ........................................... 204/195 R
[58] Field of Search ............................... 204/195 R

[56] References Cited

U.S. PATENT DOCUMENTS

| | | | |
|---|---|---|---|
| 2,862,859 | 12/1958 | Grosskopf | 204/195 R X |
| 3,493,484 | 2/1970 | Berg et al. | 204/195 R |
| 3,776,832 | 12/1973 | Oswin et al. | 204/195 R |
| 3,793,158 | 2/1974 | Hamilton | 204/195 R X |
| 3,824,167 | 7/1974 | Oswin et al. | 204/195 R |
| 3,886,058 | 5/1975 | Barna | 204/195 R X |
| 3,909,386 | 9/1975 | Oswin et al. | 204/195 R |
| 3,992,267 | 11/1976 | Oswin et al. | 204/1 T |
| 4,017,373 | 4/1977 | Shaw et al. | 204/195 R |
| 4,025,412 | 5/1977 | LaConti | 204/195 R |
| 4,036,724 | 7/1977 | Binder et al. | 204/195 R |
| 4,132,616 | 1/1979 | Tantram et al. | 204/195 R X |

Primary Examiner—G. L. Kaplan

[57] ABSTRACT

A wick system for an electrochemical cell is provided to assure the connection between the electrodes of the cell. The wick system of the invention absorbs electrolyte and by capillary action provides a continuous electrolyte path between the electrodes. The wick may be in the form of a substantially flat piece extending in one plane for those cells having all electrodes positioned at one end thereof. Alternatively, the wick may be substantially tubular to extend from one end of a cylindrical electrolyte containing chamber to another, for a cell having electrodes positioned at each end thereof. Additionally, the wick may extend from one end of the cell to the other in a folded bellows-like form. In any of the forms, the wick system allows for a continuous operation of the cell, even with reduced electrolyte content, and regardless of the three-dimensional orientation of the cell, by absorbing electrolyte and maintaining electrolytic contact.

6 Claims, 4 Drawing Figures

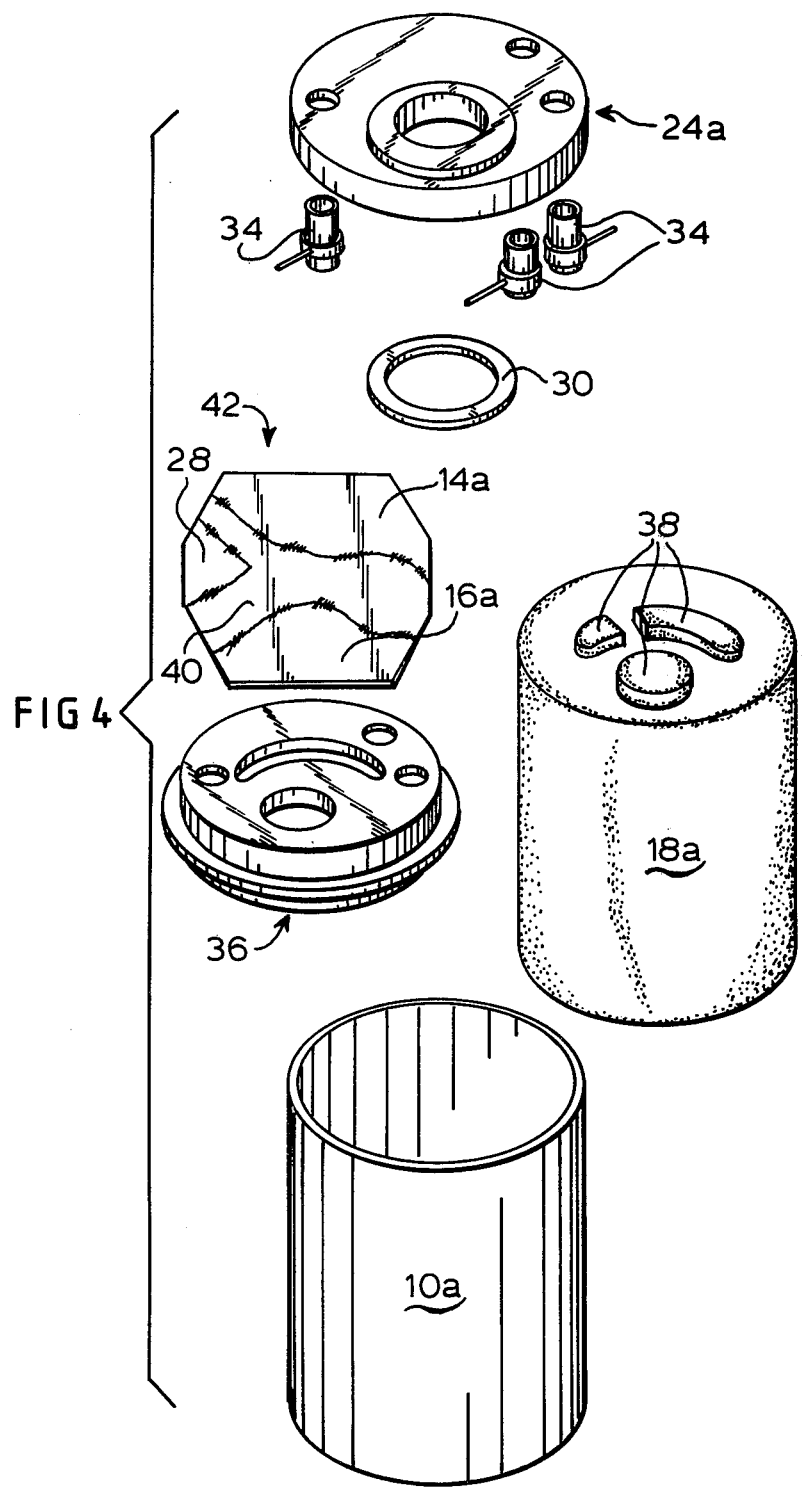

GAS DETECTION UNIT

BACKGROUND OF THE INVENTION

This invention relates generally to an electrochemical cell for use in a gas detector unit. More particularly, this invention relates to a wick system useful in the functioning of the cell in that it provides for continuous and assured contact of the electrolyte with the electrodes of the cell. The wick is comprised of a wettable material which absorbs electrolyte, and by capillary action assures the continuity between electrodes. Thus, as the gas detector unit is used over a period of time and the quantity of electrolyte diminishes, the cell will still operate because the wick continues to absorb and carry the electrolyte to the electrodes and maintains a continuous path between them. Moreover, the wick of the invention utilizes the internal vapor pressure of the electrolyte and will compensate for any water loss in those instances where an aqueous electrolyte system is being utilized.

This invention is an improvement over the inventions described in U.S. Pat. Nos. 3,992,267, issued Nov. 16, 1976; 3,824,167, issued July 16, 1974; 3,776,832, issued Dec. 4, 1973 and 3,909,386, issued Sept. 30, 1975. Each of these patents are incorporated by reference in their entirety herein. In addition, this invention is related to the invention disclosed in co-pending application Ser. No. 170,367 filed simultaneously herewith.

In the past, most electrochemical gas sensors utilizing a liquid electrolyte could only be used when maintained in one stabilized position. The sensor had to be oriented so as to make sure that all of the electrodes were in continuous contact with the electrolyte. As will be appreciated, the sensors of the past, subject to these limitations, where not properly operable in conditions where large amplitude vibrations might be present. Such vibrations, as will be understood, can momentarily isolate one or more of the electrodes from the electrolyte causing surges in the sensor response. Attempts to overcome these problems include utilizing a packing filling the entire content of the electrolyte cavity. While such a system provides a continuous contact between the electrodes, it reduces the quantity of electrolyte which may be introduced into a sensor of any given size, and because of the high absorbent qualities of the packing, it tends to disperse the electrolyte more or less uniformly throughout the cavity or container for the electrolyte. In the case of an aqueous electrolyte, such dispersed electrolyte will tend to degrade sensor performance as the sensor loses water by evaporation to dry sampled gas. Also, a small shrinkage in the volume of the packing will cause it to pull away from one or more of the electrodes and cause the sensor to cease functioning.

By contrast, the present invention through the use of the wick system, in accordance herewith, effectively provides appropriate contact on a continuous basis between the electrodes without excessively dispersing the electrolyte. Moreover, the electrochemical sensor, incorporating the invention herein is independent of its attitude and is not affected by environmental conditions such as excessive vibration or movement during the functioning thereof.

DETAILED DESCRIPTION OF THE INVENTION

With the invention herein, a thin sheet of an electrolyte wettable material is utilized, for example in contact with all electrodes adjacent the electrolyte chamber. Satisfactory results have been achieved, in accordance herewith, and under satisfactorily and economically attractive conditions in commercial scale operations using a woven or non-woven polyolefin cloth or a sintered polyolefin sheet comprised of particles of the thermoplastic sintered into such a sheet to provide the porous property required to give the capillary action desired between the electrodes. Other materials which may be useful in accordance with this invention are glass fiber filter paper, felt, wool, other polymeric materials such as polyesters, for example, and other wettable, porous materials, It will be appreciated that the material will be selected in accordance with the nature of the electrolyte being utilized. The material must be such that it will not be degraded by the electrolyte. For example, a glass fiber sheet may be utilized with a sulfuric acid electrolyte. The material will be relatively thin, as discussed above, and preferably within the range of between about 0.002 inches–0.150 inches.

The form of the wick may be of a variety of configurations depending upon the configuration of the sensor itself. For example, some sensors provide for the positioning of the electrodes all at one end of the electrolyte cell and generally in a single plane. With this arrangement, the wick of the invention will be flat and also in one plane and positioned adjacent to the electrodes involved. For the gas detector unit, in accordance herewith, it is preferable to utilize three electrodes, including a working electrode, a counterelectrode and a reference electrode, as discussed in U.S. Pat. No. 3,776,832. The third or reference electrode is utilized to maintain a fixed relative potential between the working and the reference electrode, as described in U.S. Pat. No. 3,776,832.

In some configurations of gas detection units, the units are configured to provide the working electrode at one end of an electrolyte chamber and the counter and reference electrodes at the opposite end. In those instances where such a configuration is utilized, it is necessary to provide a wick configuration which will extend from one end of the electrolyte chamber to the opposite end. Such electrolyte configurations include a wick extending from one end of the chamber while encompassing the entire internal volume to the opposite end. It may be tubular for a cylindrical chamber, with the wick extending along the walls of the chamber from one end to the other and comprised of, for example, a molded sintered polyethylene sheeting material with a portion extending along an electrode at each end of the chamber. The sintered material may be heat sealed for appropriate contact with the electrodes. A further configuration may be in the form of a folded bellows-shaped flat piece of material extending from one end of the chamber to the opposite end and heat sealed at either end for fixed contact. Such an arrangement provides for efficient contact of the electrolyte and electrodes in the chamber along its entire extent and causes the wick to carry the electrolyte material by capillary action to the electrodes involved. Such a "bridging wick" need not adhere to the inside surface of the sensor electrolyte chamber, but should be long enough to contain one or more folds so as to maintain contact with the electrolyte, and avoid pulling away from the electrodes.

As discussed above, in any one of the forms described for the wick of the invention, the wicking material remains in continuous contact with the bulk of the electrolyte. Once the electrodes and wick have been thoroughly wetted by the electrolyte, the internal vapor pressure of the electrolyte will more than compensate for any water loss to the environment through the electrodes during use of the sensor unit.

With the foregoing and additional objects in view, this invention will now be described in more detail, and other objects and advantages thereof will be apparent from the following description, the accompanying drawings, and the appended claims.

DESCRIPTION OF THE DRAWINGS

FIG. 4 is an exploded perspective view of an electrolyte sensor chamber utilizing a molded sintered wick of the invention.

Figure 1:
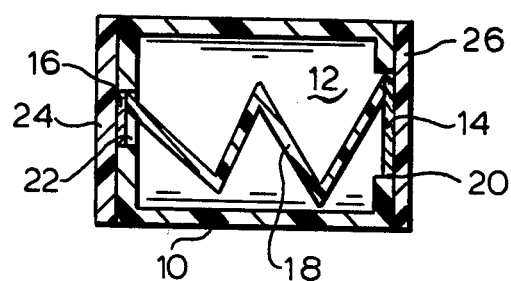
FIG. 1 is a longitudinal sectional view of an electrolyte chamber illustrating the invention in the form of a bridging wick extending from one end of the chamber to the opposite end.

Referring to the drawings in which like reference characters refer to like parts throughout the several views thereof, an embodiment of apparatus for practicing the invention is shown in the form of a tubular or rectangular sensor unit 10 with an electrolyte chamber 12 which contains electrolyte for establishing an electrical connection between electrodes 14, 16 positioned at each end of the chamber. A wick 18 is shown in the form of a flat folded sheeting material with a portion 20 thereof extending along and heat sealed to electrode 14, and a portion 22, thereof extending along the heat sealed to electrode 16. As will be appreciated, chamber 12 is enclosed at each end by end plates 24, 26 and will have the appropriate electrical connections and provision for the introduction of a gas to be sensed by the cell adjacent electrode 16. Reference is made, in this connection, to the structure as generally shown in U.S. Pat. No. 3,909,386.

At any rate, with the embodiment shown in FIG. 1, a "bridging wick" is shown which extends from electrode 16 to electrode 14 positioned at each end of the chamber. As will be understood, there may be two electrodes in the form of a counter electrode and a reference electrode (not shown) at the position of electrode 14. In such a circumstance, the portion 20 of the wick 18 will extend as shown in FIG. 1 along and touch both electrodes.

Figure 2:
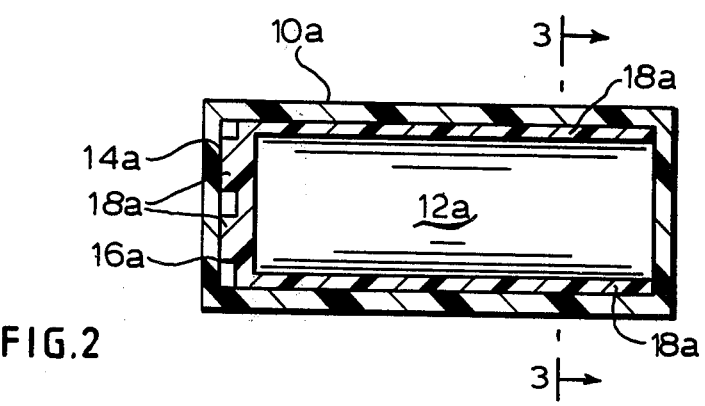
FIG. 2 is a longitudinal sectional view of a further embodiment of the invention illustrating the wick of the invention in cylindrical form.
Figure 3:
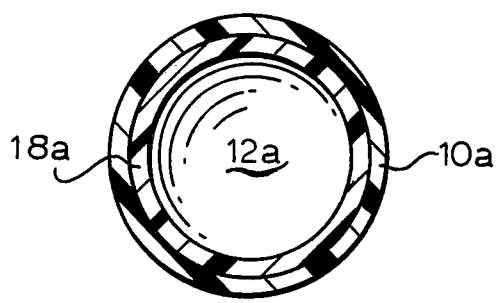
FIG. 3 is an enlarged cross-sectional view taken along line 3—3 of FIG. 2.

Referring now to FIGS. 2, and 3, the wick 18a shown is tubular in shape and extends along the cylindrical walls of electrolyte chamber 12a of sensor unit 10a. In this arrangement, the electrodes 14a, 16a are positioned at one end of electrolyte chamber 12a. The tubular wick, by extending along the entire length of the chamber, is exposed to the electrolyte at any portion of the length of the chamber and by capillary action carries the electrolyte to and adjacent each of the electrodes 14a, 16a positioned at one end of the chamber. Moreover, once the electrolyte has wetted the wick and the electrodes 14a, 16a, a proper contact is maintained by the wick which is wetted by internal vapor pressure (between the electrodes) regardless of the amount of electrolyte remaining in the chamber.

Referring now to FIG. 4, an exploded perspective view of an electrolyte gas diffusion sensor cell is shown with a molded sintered wick 18a which may be comprised of particles of polyethylene or polypropylene, for example, and extends along the length of the cylindrical housing 10a. In this arrangement, the electrode is in the form of three electrodes 14a, 16a and 28 positioned in one plane on flat substrate 42, and separated by a non-conducting material 40. The electrode 28 is the reference electrode for maintaining the appropriate desired potential on working electrode 14a. As can be seen, the molded sintered wick is configured with integral extensions 38 which extend through electrode plate 36 to make contact with the electrodes. End plate 24a is shown with terminals 34 extending therethrough for contact with the individual electrodes.

As will be appreciated, with this arrangement, the molded sintered wick 18a surrounds and extends the entire length of the electrolyte chamber and is in constant contact with whatever quantity of electrolyte may be present, whether the electrolyte is an aqueous electrolyte or of a gel-like consistency. At any rate, there is substantial and complete contact between the electrolyte and the electrodes while contact is maintained on a continuous basis regardless of the orientation of the sensing unit when it is being held or utilized for sensing. Thus, it will be appreciated, with units of this kind which are hand-held the user need not be concerned with the proper orientation thereof in order to obviate surges in the sensor response.

Obviously, all of the above serves to make the methods and apparatus herein highly advantageous commercially, not only in those instances where the sensors are to be used in a fixed position, because of the continuous utilization of whatever electrolyte content is available in the chamber by the wick system in accordance herewith; but also, in those instances where the sensor is used for breath samples by a highway patrol, for example, it is not necessary for a patrolman to be concerned with the orientation of the sensor in order to provide a proper signal in the awkward and sometimes disagreeable circumstances which this entails.

While the methods and apparatus herein disclosed form preferred embodiments of this invention, this invention is not limited to those specific methods and apparatus, and changes can be made therein without departing from the scope of this invention, which is defined in the appended claims. For example, the wick need not be in the form of a folded bellows-like flat sheet but may be, for example, in helical form extending from one end of the sensor chamber to the other. Also, it may be desirable to form the molded sintered wick in the form of intermittent strips extending along the walls of the chamber as opposed to a solid cylindrical wick, if material costs are important, with the individual strips being joined to a single portion at one end of the chamber.

What is claimed is:

1. An electrochemical gas detection unit, comprising
   (a) a cylindrical electrolyte chamber;
   (b) a working electrode with one surface exposed to said electrolyte chamber;
   (c) a counterelectrode with one surface exposed to said electrolyte chamber;

(d) a reference electrode with one surface exposed to said electrolyte chamber;
(e) said working, said counter and said reference electrodes are positioned in a single plane at one end of said chamber;
(f) means interconnecting said working electrode and said reference electrode for maintaining a preselected fixed reference potential on said working electrode;
(g) intake means for exposing said working electrode to a gas to be detected;
(h) wick means positioned entirely within said chamber;
(i) said wick means is in the shape of a cylinder extending along the length of said chamber and closed at one end for contacting electrolyte in said chamber;
(j) said closed end of said wick means positioned entirely within said single plane for interconnecting said working electrode, said counterelectrode and said reference electrode; and
(k) said wick means being comprised of a material which is wettable by an electrolyte introduced into said chamber.

2. The apparatus of claim 1, further characterized by
(a) said wick means being of a thickness within the range of between about 0.002 inches and 0.150 inches.

3. The apparatus of claim 1, further characterized by
(a) said wick means being comprised of a material selected from the group consisting of a woven or linear polymeric material, a sintered molded polymeric material, glass fiber, and wool.

4. An electrochemical gas detection unit, comprising
(a) a cylindrical electrolyte chamber;
(b) a working electrode with one surface exposed to said electrolyte chamber;
(c) a counterelectrode with one surface exposed to said electrolyte chamber;
(d) a reference electrode with one surface exposed to said electrolyte chamber;
(e) means interconnecting said working electrode and said reference electrode for maintaining a preselected fixed reference potential on said working electrode;
(f) intake means for exposing said working electrode to a gas to be detected;
(g) said working electrode positioned at one end of said chamber;
(h) said counterelectrode and said reference electrodes positioned at the end of said chamber opposite said working electrode;
(i) substantially flat and thin wick means positioned entirely within said chamber;
(j) said wick means has a plurality of folds therein and extending between said working electrode at one end of said chamber and said counterelectrode and reference electrode at the opposite end thereof; and
(k) said wick means being comprised of a material which is wettable by an electrolyte introduced into said chamber.

5. The apparatus of claim 4, further characterized by
(a) said wick means being of a thickness within the range of between about 0.002 inches and 0.150 inches.

6. The apparatus of claim 4, further characterized by
(a) said wick means being comprised of a material selected from the group consisting of a woven or linear polymeric material, a sintered molded polymeric material, glass fiber, and wool.

* * * * *